United States Patent [19]

McElhenney

[11] Patent Number: 5,152,762
[45] Date of Patent: Oct. 6, 1992

[54] CURRENT LEAKAGE CONTROL FOR ELECTROSURGICAL GENERATOR

[75] Inventor: Jay J. McElhenney, Laguna Hills, Calif.

[73] Assignee: Birtcher Medical Systems, Inc., Irvine, Calif.

[21] Appl. No.: 614,275

[22] Filed: Nov. 16, 1990

[51] Int. Cl.$^5$ .............................................. A61B 17/39
[52] U.S. Cl. ...................................................... 606/35
[58] Field of Search ............................... 606/35, 38–40

[56] References Cited

U.S. PATENT DOCUMENTS

| | | | |
|---|---|---|---|
| 3,683,923 | 8/1972 | Anderson | 606/35 |
| 4,094,320 | 6/1978 | Newton et al. | 606/35 |
| 4,102,341 | 7/1978 | Ikuno et al. | 606/35 |
| 4,437,464 | 3/1984 | Crow | 606/35 |
| 4,462,369 | 5/1987 | Ensslin | 606/35 |
| 4,727,874 | 3/1988 | Bowers et al. | 606/38 |

FOREIGN PATENT DOCUMENTS 3544460 6/1987 Fed. Rep. of Germany ........ 606/35

*Primary Examiner*—Lee S. Cohen
*Attorney, Agent, or Firm*—John R. Ley

[57] ABSTRACT

A current leakage control circuit regulates the output power of an electrosurgical generator to limit the amount of leakage current. The leakage current is monitored with a differential transformer which has the output and return leads of the electrosurgical generator as first and second windings. A third or sense winding produces a control signal whenever the currents in the output and return leads are not equal, thus indicating current leakage. The control signal is compared to a predetermined maximum safe level of leakage current. If this predetermined level is exceeded, a power control feedback loop of the electrosurgical generator reduces the output power to a sufficiently lower level to reduce the leakage current within a maximum acceptable limit.

9 Claims, 2 Drawing Sheets

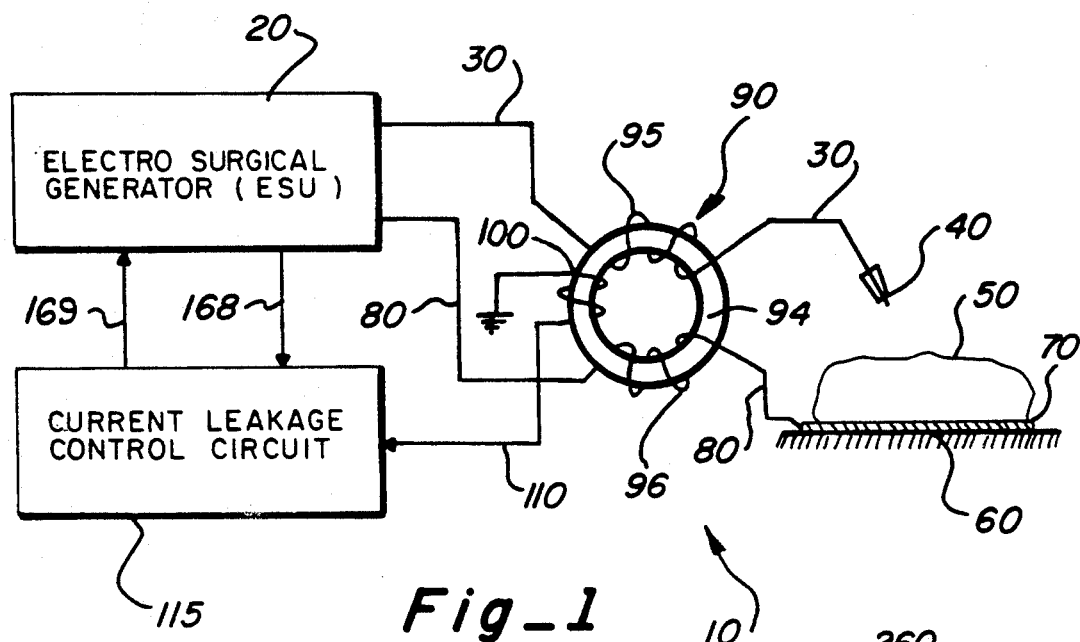
Fig_1
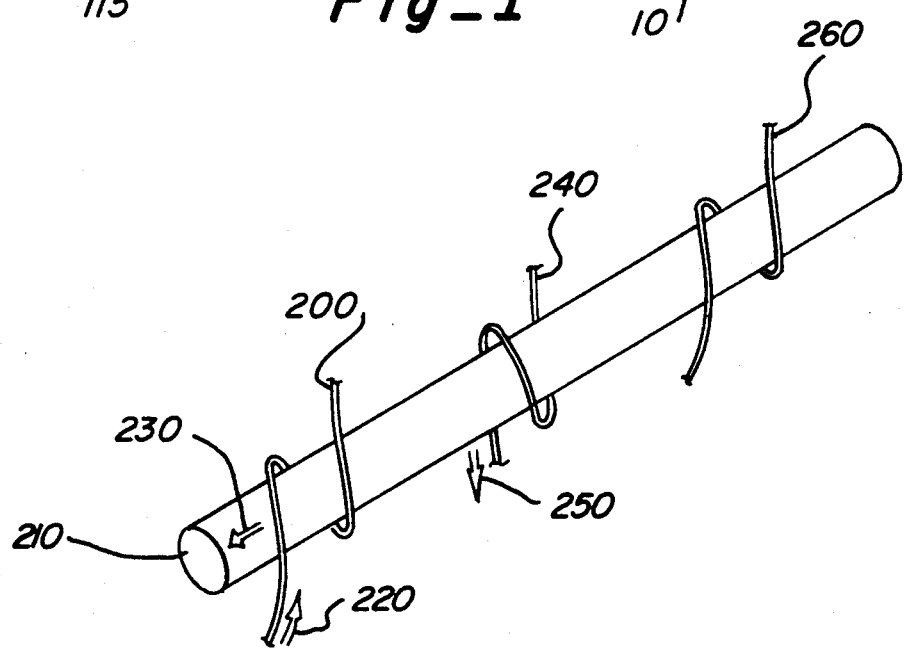
Fig_2
PRIOR ART

CURRENT LEAKAGE CONTROL FOR ELECTROSURGICAL GENERATOR

This invention pertains to the field of electrosurgery and more particularly to controlling of the output power of an electrosurgical generator unit (ESU) to reduce leakage currents.

BACKGROUND OF THE INVENTION

Electrosurgery is the application of a high frequency electrical current to a surgical site on a patient for the purpose of tissue cutting and/or coagulation. The high frequency current that is generated by an ESU is applied to the patient's body from an active electrode which is held by the surgeon, and is collected from the patient's body at a dispersive electrode. A relatively small contact area of the active electrode to the tissue causes a high current density entering the patient at the surgical site. This high current density causes intense localized heating, arcing and other effects, to achieve the cutting and/or coagulation. The dispersive electrode collects the current from the patient's body and returns it to the ESU to complete the electrical circuit. The dispersive electrode is of a significant size so that the density of the current it collects is low enough to avoid any surgical or heating effect.

If the current in the patient's body ever develops a high current density during its passage through the body, localized tissue heating will occur and a burn will develop. This situation can occur if the current is allowed to exit the patient's body at a location other than the dispersive electrode. Such current is known as a leakage current. A burn from leakage currents can be quite severe as the patient is anesthetized and cannot react to the burn. The burn area is frequently covered so the doctor or surgical attendants will not see it until it is too late to take corrective action. Another potential for leakage current burns is to the surgeon from the active electrode or the conductors which supply the high frequency, high voltage electrosurgical energy. Leakage currents in this case may harm or burn the surgeon or one of the surgical attendants in contact with the active electrode or its supply conductor. It is for this reason that leakage or alternate path currents in electrosurgery are of considerable concern.

The first ESUs were of a ground-referenced design. Being ground referenced, the return for the ESU and the dispersive electrode were both connected to earth ground. The ground referenced arrangement was satisfactory provided that no other point on the patient was ground-referenced. For example, if a monitoring electrode was on the patient's body during the surgical procedure, and the monitoring electrode is referenced to ground, some portion of the electrosurgical current would flow to ground through the monitoring electrode, instead of the preferred path back through the dispersive electrode. Since monitoring electrodes may be small, the current density through them may be sufficient to develop a high enough density to cause a burn. An even worse condition occurs if the generator connection to the dispersive electrode is accidentally broken. With no direct current path back to the ESU, all of the electrosurgical current will travel through alternate grounded paths, such as through the monitoring electrodes and the surgical table, and severe burning is likely to result.

In an effort to reduce the risks associated with the ground-referenced ESUs, the power output circuit of the ESU was isolated from ground. Output isolated ESUs were a significant step in reducing the risks associated with alternate path burns, because the electrosurgical current exiting the patient was more likely to flow through the dispersive electrode than any ground referenced points on the patient, in returning to the ESU. If the generator connection to the dispersive electrode became disconnected, a significant amount of the electrosurgical current flow from the ESU would stop.

Although an improvement over the previous ground-referenced ESUs, the problem with isolated output ESUs was that the isolation from ground was not perfect. At the relatively high frequencies of electrosurgical current, e.g., 500 kiloHertz to 1 megaHertz, any stray capacitance to ground presents a ground referenced signal path. Furthermore, the amount of stray capacitance required to create a significant path for ground-referenced currents is not great. Although alternate path currents are less than those flowing if the ESU was ground-referenced, the potential still remains for significant patient and alternate path burns.

An improvement to help minimize alternate path currents in isolated ESUs involved the use of a differential transformer in the output circuit, as shown in U.S. Pat. No. 4,437,464. The electrosurgical current supplied to the active electrode flows through one winding on the transformer core, and the current from the dispersive electrode flows through the other winding. When the currents in the two windings are equal, as would be the case when no alternate path currents flow, the flux from both currents cancels, and transformer presents very little insertion loss or impedance to the flow of electrosurgical current. If a significant alternate path current does flow, the imbalance creates a flux in the core of the differential transformer causing a large insertion loss. The insertion loss increases the impedance and reduces the amount of current flowing to the active electrode. Thus, the current flow to the patient is reduced, also causing a decrease in the alternate path or leakage current. Although this approach reduces leakage current, it may not be sufficient to reduce the leakage current below a maximum acceptable safe level, for example one hundred fifty milliamps.

Another improvement which provides an alarm under conditions of excessive leakage current with isolated ESUs, or which terminates the delivery of all electrosurgical power, is disclosed in U.S. Pat. No. 3,683,923. A sensing winding on the differential transformer senses the imbalance in the current flowing in the active lead and the return lead. Upon sensing a sufficient imbalance in the current sensed, an alarm circuit is triggered and a warning is given to the operator. In addition, a relay may be simultaneously or alternatively activated to terminate the flow of current to the patient. The operator must then take corrective action such as reducing the power level or attempting to eliminate the problem causing current leakage, as well as reactivating the ESU.

It is against this background that the further significant improvements and advancements of the present invention have evolved in the field of controlling leakage current in isolated ESUs.

SUMMARY OF THE INVENTION

One of the significant aspects of the present invention is an improved technique of regulating the output power of an ESU to limit the amount of leakage current. The amount of current leakage is sensed and used to reduce and maintain the output power to limits at which the leakage current is within predetermined acceptable limits.

In accordance with one of its major aspects, a current leakage sense control signal is derived from a current leakage sense means which determines any imbalance between the current supplied from an electrosurgical generator and the current returned to the electrosurgical generator. The control signal is utilized by a control means which controls a power control feedback loop means of the electrosurgical generator to reduce the output power supplied by the electrosurgical generator when the current leakage sense signal exceeds a predetermined set point at which the maximum acceptable limit of leakage current is defined. Preferably, the current leakage sense means comprises a sense winding of a transformer which has two other windings which each carry the supplied and the returned current. The two windings are arranged such that unequal currents in the two windings will result in a non-zero control signal. The control signal is supplied to power control feedback control loop means to control the output power of the electrosurgical generator.

In accordance with another of its major aspects, a method of limiting the electrosurgical power applied to an active electrode to avoid leakage currents of magnitudes greater than a maximum acceptable level is provided. The method includes steps of generating electrosurgical power in response to a requested power level, applying the electrosurgical power by supplying current to the active electrode and receiving return current from a dispersive electrode, sensing an amount of imbalance between the amount of electrosurgical current supplied and received, and reducing the level of the electrosurgical power applied to maintain the sensed imbalance of current at or below the maximum acceptable level.

A more complete understanding of the nature of the present invention and its advantages and improvements can be obtained from the following detailed description of a presently preferred embodiment of the invention taken in conjunction with the accompanying drawings, briefly described below, and from the appended claims.

DETAILED DESCRIPTION OF THE DRAWINGS

FIG. 1 is a generalized block diagram of an ESU, an active and a return electrode, a leakage current sensing transformer, and a leakage current control circuit of the present invention.

FIG. 2 is an illustration of the prior art physical relationship between the current flowing in coils around a magnetic core and the magnetic flux in the core, for explaining the operation of a transformer of the circuit shown in FIG. 1.

DETAILED DESCRIPTION

Figure 3:
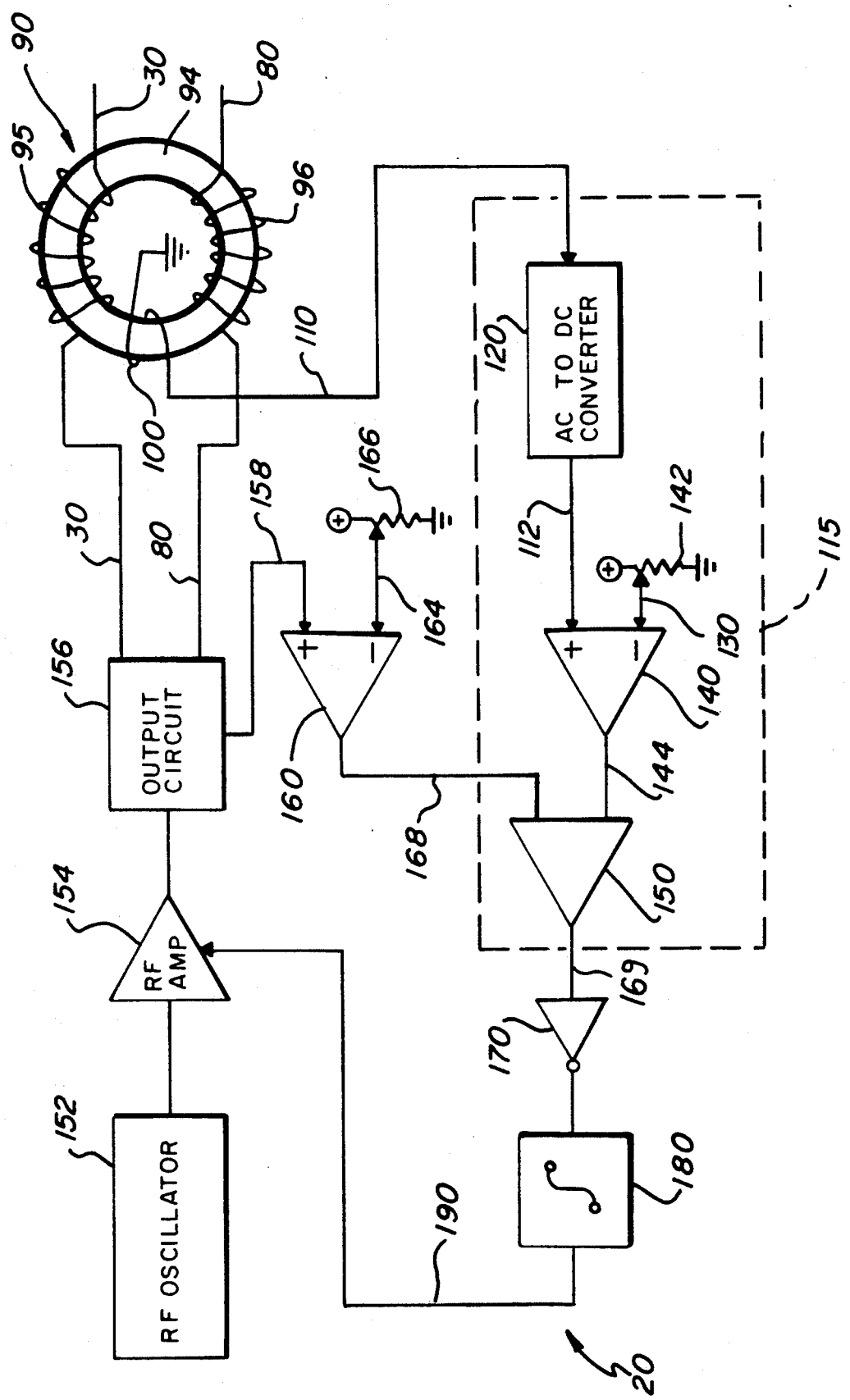
FIG. 3 is a more detailed block and schematic diagram of portions of FIG. 1.

An electrosurgical system 10 which incorporates a leakage current control circuit 115 of the present invention in a portion of its power control feedback loop is shown in FIG. 1. An ESU 20 generates high frequency current for use in electrosurgery. The current is supplied to supply conductor or lead 30 which conducts the current to an active electrode 40, from which the current is applied to a patient 50. The patient 50 is typically lying on a surgical table 60 and on top of a return or dispersive electrode 70. The return electrode 70 is connected to a return conductor or lead 80 which returns the electrosurgical current to the ESU 20, thus completing the electrical circuit.

A magnetic core differential transformer 90 provides a magnetic flux under leakage current circuit imbalance conditions, as is explained more completely in U.S. Pat. No. 4,437,464. A first winding 95 around a core 94 of the differential transformer 90 is formed by the output lead 30 and conducts the current supplied to the active electrode. A second winding 96 is formed by the return lead and conducts the current flowing in the return lead 80. The magnetic flux flowing in the transformer is sensed by a sense winding 100 which supplies a differential control signal 110 to the current leakage control circuit 115 The current leakage control circuit 115, in conjunction with the normal power control feedback circuit of the ESU, limits and controls the amount of current generated by the electrosurgical generator 20.

FIG. 2 illustrates the relationship between current flow and magnetic flux in a transformer, such as that shown at 90 in FIG. 1. A wire 200 forms a first coil around a magnetic core 210. If a current flows through the wire 200 in the direction of the arrow 220, a magnetic flux will form in the core in the direction shown by the arrow 230, according to basic principles of electromagnetism. As a result of the magnetic flux shown by the arrow 230, another wire 240 formed as a second coil wrapped in the opposite direction around the core 210 will have a resulting current induced in it in the direction of the arrow 250. The current in the direction of arrow 250 will be of equal value to the current flowing through the wire in the direction shown by the arrow 220, if the number of individual coils of the wires 200 and 240 are the same. If, for example, each of the wires 200 and 240 had current flowing in them from a separate source but in the same direction, each coil would create a magnetic flux in the core. If the currents were equal, the opposite fluxes from each coil would cancel. If the currents were unequal, then the net magnetic flux would be non-zero and would induce a resulting current in a third wire 260 formed as a third winding around the core.

As can be seen in FIG. 1, the winding 95 which conducts the current from the supply lead 30 induces a magnetic flux in the counterclockwise direction in the core 94, as viewed. The winding 96 which conducts the current of the return lead 80 in FIG. 1 causes a magnetic flux in the clockwise direction in the core 94, as viewed. If the number of coils of the windings 95 and 96 are equivalent and the currents flowing in leads 30 and 80 are equal, then the two induced magnetic fluxes will be equal. Furthermore the two fluxes will be opposing one another and will cancel, resulting in a net magnetic flux of zero in the core 94. If, however, the current flowing in the supply lead 30 is greater than the current flowing in the return lead 80 because of current leakage, then a net finite non-zero magnetic flux will result. This non-zero magnetic flux will induce a current flow in the sense winding 100. The signal from the sense winding 100 is a current leakage sense signal or a differential control signal 110, and this signal represents the amount of difference in the currents flowing in the supply and return leads 30 and 80, respectively.

The differential control signal 110 is applied to the current leakage control circuit 115, as shown in FIGS.

1 and 3. The currents flowing in both the supply lead 30 and the return lead 80 are flowing at the electrosurgical frequency in the range of 500 kiloHertz to 1 megaHertz. Therefore, the differential control signal 110 will be an AC signal at a similar frequency. The differential control signal 110 is supplied to an AC to DC converter 120 to obtain an output DC signal 112 proportional to the amplitude of the AC signal 110. The AC to DC converter 120 may utilize a variety of different conversion techniques. For example, the converter 120 may be more sensitive to peak values or to RMS values of the AC control signal 110.

The magnitude of the DC output signal 112 is linearly proportional to the magnitude of the control signal 110, and the control signal 110 is proportional to the amount of leakage current, as explained above. The signal 112 is applied to the positive input terminal of a differential amplifier 140. A predetermined DC signal 130 representative of a set point is applied to the negative input terminal of the differential amplifier 140. The magnitude of the DC signal 130 is selected by adjustment of a potentiometer 142, and the predetermined level of the signal 130 represents a maximum acceptable safe level of leakage current.

The gain of the differential amplifier 140 is unity. Therefore, an output signal 144 of the differential amplifier 140 will be positive whenever the sensed leakage current (represented by the signal 112) exceeds the maximum acceptable safe level of leakage current (represented by the predetermined set point established by the signal 130). Otherwise the output signal 144 will be negative. The output signal 144 of the differential amplifier 140 is applied to one input terminal of a conventional maximum selector circuit 150. A second input terminal of the maximum selector circuit 150 is connected to an output terminal of a power control differential amplifier 160. The power control differential amplifier 160 is part of a conventional closed loop feedback power control arrangement of the ESU 20.

Closed loop feedback power control arrangements, or power control feedback loops, are widely used in ESUs, and take a variety of different configurations. One relatively complex power control feedback loop is disclosed in U.S. Pat. No. 4,727,874. A generalized form of a power control feedback loop for the ESU 20, which uses the current leakage control circuit 115 is shown in FIG. 3. In very basic terms, the ESU includes a radio frequency (RF) oscillator 152, a RF amplifier 154 and an output circuit 156. The RF oscillator 152 generates the RF signal which becomes the electrosurgical signal after the RF amplifier 154 amplifies it. The output circuit 156 supplies the electrosurgical signal to the supply lead 30 and receives the return current from the return lead 80. A signal 158 is supplied from the output circuit 156 which represents and is proportional to the amount of output power supplied from the ESU 20. The signal 158 is applied to a positive input terminal of the power control differential amplifier 160. The other signal applied to the negative input terminal of the power control differential amplifier 160 is an output power requested signal 164. The output power requested signal 164 is related to the power requested by the operator and is established by the adjustment of a front control panel adjustment potentiometer 166.

The power control feedback loop in the electrosurgical generator 20 attempts to maintain an output signal 168 of the differential amplifier 160 at a zero steady-state value, by controlling the gain of the RF amplifier 154. With the present invention, the power control feedback loop will also consider the effect of leakage current relative to the set point, which is represented by the signal 144, to regulate the output power of the ESU 20.

The maximum selector circuit 150 selects the most positive one of its two input signals 144 or 168 to present as an output signal at its output terminal. When no leakage current is sensed, the output signal 144 of the leakage sense differential amplifier 140 will be a large negative value. The output signal 168 of the power control differential amplifier 160 will normally be at or near a zero value. Therefore, when no leakage current is sensed, the selector circuit 150 will supply the signal 168 as its output. An output signal 169 of the maximum selector circuit 150 is applied to an invertor 170 which changes the polarity of the signal. The output signal of the invertor is supplied to an integrator 180 which integrates the signal and supplies the integrated signal as a gain control signal 190. The gain control signal 190 of the integrator 180 is applied to the RF amplifier 154 which controls the amplifier 154 to establish the magnitude of the electrosurgical signal available from the ESU.

A typical power control feedback loop would supply the output signal 168 from the differential amplifier 160 directly to the input of the invertor 170. The present invention inserts an additional control provision of the current leakage control circuit 115 in the power control feedback loop. The current leakage control circuit 115 modifies the normal functionality of the power control feedback loop to control the output power of the ESU as follows.

When leakage currents are low, and the normal control loop is at steady state, the output signal 168 of the differential amplifier 160 will be zero and the output signal 144 of the leakage sense differential amplifier 140 will be negative. Thus, the zero value of the signal 168 is present at the output terminal of the maximum selector 150 as the signal 169 and is carried through to the integrator 180. The integrator will therefore not change its output value and the output power of the ESU will remain unchanged. If, however, the output power measured signal 158 were to increase and exceed the output power requested signal 164, then the output signal 168 of the power control differential amplifier 160 would become positive and would cause the integrator 180 to supply a decreased output signal to the RF amplifier 154, thus causing the RF amplifier to decrease the output power of the ESU until the output power measured signal 158 equals the output power requested signal 164 and the output signal of the power control differential amplifier 160 was returned to a zero value. On the other hand, if the output power measured signal 158 were to decrease to a value less than the output power requested signal 164, the output signal 168 of the power control differential amplifier 160 would become negative and cause the integrator 180 to supply an increased output signal to the RF amplifier 154, thus causing the RF amplifier to increase the output power of the ESU until the output power measured signal 158 equals the output power requested signal 164 and the output signal of the power control differential amplifier 160 returns to zero. Thus under leakage current conditions which are within the maximum acceptable limits, the normal power feedback control functions of the ESU are unmodified.

Under leakage current conditions which exceed the maximum acceptable limits, the current leakage control circuit 115 in the feedback power control loop functions as follows. The leakage current will cause a flux in the core 94 of the transformer 90, which will be detected by the sense winding 100. A non-zero differential control signal 110 will result. The converter 120 converts the signal 110 to a related DC signal 112. If the signal 112 exceeds the predetermined DC set point signal 130, the leakage sense differential amplifier 140 will supply a positive output signal 144. The positive output signal 144 will be selected by the maximum selector 150, will be inverted by the invertor 170, and will cause the gain control signal 190 from the integrator 180 to decrease, thus causing the RF amplifier 154 to decrease the output power of the ESU until the resulting leakage current has reduced to a level such that the leakage sense differential amplifier 140 will have a zero value. The output power of the generator is therefore regulated to a level which constrains the leakage current to the predetermined maximum acceptable value, e.g., one hundred forty milliamps. The action of the current leakage control circuit 115 thus overcomes the normal feedback power control function to limit the electrosurgical output current to that maximum acceptable value which would be incapable of producing alternate path burns or effects. The effect of the leakage current control circuit 115 is to limit the output power of the ESU without disabling the ESU.

The power control feedback loop is thus controlled by two different sensing signals, the leakage current signal 110 and the output power requested signal 164. Only when significant leakage currents attempt to flow does the leakage sense circuit take over control of the electrosurgical output current. The present invention allows for a smooth transition between these two different control loop input signals with no abrupt change in output level when the control is shifted between the two input signals.

Significant leakage currents only flow when two conditions are satisfied. First, a path for the leakage current must exist. This will manifest itself as a ground-referenced point, e.g., a grounded monitoring electrode, a grounded operating room table, or even a surgeon himself. The second condition to be satisfied is the existence of enough electrosurgical potential, or voltage, to drive the leakage current. The first condition is a function of operating room set-up. The second condition is a function of the requested power setting (output power requested) on the ESU and the load on the ESU. Since a high voltage is required to drive a leakage current, significant leakage currents will only flow when the generator is activated open circuit (when the active electrode is held away from the tissue). Under these conditions, a large voltage exists on the active electrode and no primary electrosurgical current flows. As soon as the electrode is brought close enough to the tissue to allow primary electrosurgical current to flow, the high voltage potential reduces greatly. Thus, significant leakage currents will flow primarily only when the electrode is activated in an open circuit condition. The amount of leakage current that will flow is also a function of the requested power setting. If a relatively lower power is requested, lower leakage currents will flow as the electrosurgical output is less regardless of its loading condition.

Therefore, the current leakage control circuit 115 will only function when several conditions are met. The electrode must be held far enough away from the tissue to prevent primary electrosurgical current from flowing, and the requested power must be sufficiently great. As soon as the electrode is brought close enough to the tissue to allow primary electrosurgical current to flow, leakage current will be reduced and the current leakage control circuit 115 will smoothly return control of the output power over to the normal power control feedback circuitry. At this point the output power is unrestricted by the current leakage control circuit 115, and full requested power is available to be delivered to the tissue. Thus, a smooth transition is provided between power control based upon the leakage control circuit and current control based upon output power requested.

Since the set point of, preferably one hundred forty milliamps, does not change with output power requested, the amount of reduction of the open circuit potential by the leakage control circuit will be less when a relatively lower output power is requested. There will be a point in the requested power setting when the active electrode is activated in the open circuit condition, that the leakage control circuit will not reduce the output at all because the leakage current is less than one hundred forty milliamps. Under these conditions, the current leakage control circuit 115 does not affect the output. Under conditions where the operating room set-up is such that there are no attractive ground paths for the leakage currents to flow, the current leakage control circuit 115 similarly does not affect the output.

It therefore can be seen that the current leakage control circuit is only operative when leakage current conditions require it. The circuit continuously monitors the leakage current so that an unsafe condition will not be allowed to occur. An advantage of this invention over other existing leakage reduction techniques currently being employed, is that the current leakage control circuit continuously monitors the conditions and adapts the output power of the ESU accordingly.

A preferred embodiment of the present invention has been shown and described with a degree of particularity. It should be understood, however, that the specificity of the present description has been made by way of preferred example, and that the scope of the present invention is defined by the appended claims.

The invention claimed is:

1. In an electrosurgical system having an electrosurgical generator for supplying electrosurgical output power by delivering an output current at a predetermined frequency to a patient, a supply lead means for delivering the output current from the generator to the patient, a return lead means for returning current from the patient to the generator, and a power control feedback loop means of said generator for regulating the output power of the generator to a value approximately equal to a predetermined output power requested, the power control feedback loop means including means for supplying a power control signal representative of any difference between the output power supplied by the generator and the predetermined output power requested and regulating means for regulating the output power of the generator in response to the power control signal; and in combination therewith an improved means for controlling leakage current from the generator comprising:

current leakage sense means connected to the supply lead means and to the return lead means and operative for determining any imbalance between the current flowing in the supply lead means and the current flowing in the return lead means and for generating a current leakage sense signal related to the amount of any said imbalance;

means for supplying a predetermined set point signal representative of a predetermined maximum acceptable amount of leakage current;

determining means receptive of the current leakage sense signal and the set point signal for supplying a leakage current control signal upon the current leakage sense signal exceeding the predetermined set point signal; and selector means connected in the power control feedback loop means between the means for supplying the power control signal and the regulating means, the selector means receiving the leakage current control signal and the power control signal, the selector means operatively selecting one of the leakage current control signal or the power control signal and supplying the selected on of the signals to the regulating means to control the output power supplied by the generator both in response to the imbalance and in response to the difference between the predetermined output power requested and output power supplied by the generator by reducing the output power supplied by the generator when the imbalance exceeds the predetermined maximum acceptable amount and by regulating the output power supplied by the generator in relation to the difference between the predetermined output power requested and the output power supplied by the generator when the imbalance does not exceed the predetermined maximum acceptable amount.

2. An invention as defined in claim 1, wherein:
said selector means further selects the one of the power control signal or the leakage current control signal to control the power control feedback loop means to limit the output power supplied by the generator to a maximum value at which the leakage current does not exceed the predetermined amount.

3. An invention as defined in claim 2, wherein:
said selector means further controls the power control feedback loop means to reduce the amount of output power supplied by the generator until the imbalance is equal to or less than the predetermined amount.

4. An invention as defined in claim 1, wherein the current leakage sense means comprises:
a differential transformer including a core and a first winding and a second winding and a sense winding, each of the windings wound around the core, the supply lead means connected to conduct the delivered output current through the first winding, the return lead means connected to conduct the returned current through the second winding, the differential transformer sensing any imbalance between the currents flowing in the first and second windings and generating a current in the sense winding proportional to said imbalance, the current in the sense winding deriving the current leakage sense signal.

5. In an electrosurgical system having an electrosurgical generator for supplying electrosurgical output power at a predetermined high frequency, a supply lead means for delivering the output current from the generator to a patient, a return lead means for returning current from the patient to the generator, and a power control feedback loop means of said generator for regulating the output power of the generator to a value approximately equal to a predetermined output power requested, the power control feedback loop means comprising means for supplying a power control signal representative of a difference between the output power supplied by the generator and the predetermined output power requested and regulating means for regulating the output power supplied by the generator in response to the power control signal; the improvement comprising:

current leakage sense means connected to the supply lead means and the return lead means for determining any imbalance between the current flowing in the supply lead means and the current flowing in the return lead means and operative for generating a current leakage sense signal related to the amount of said imbalance; and control means responsive to the current leakage sense signal and operative for controlling the power control feedback loop means to reduce the output power supplied by the generator when the current leakage sense signal exceeds a predetermined value representative of a maximum amount of acceptable leakage current and to limit the output power supplied by the generator to a maximum value at which the leakage current does not exceed the predetermined maximum acceptable value and to reduce the output power supplied by the generator until the current imbalance is equal to or less than the predetermined maximum acceptable value; and wherein the control means comprises:

a differential transformer including a core and a first winding and a second winding and a sense winding, each of the windings wound around the core, the supply lead means connected to conduct the delivered output current through the first winding, the return lead means connected to conduct the returned current through the second winding, the differential transformer sensing any imbalance between the currents flowing in the first and second windings and generating the current leakage sense signal in the sense winding which is proportional to said imbalance;

converter means for converting the current leakage sense signal in the sense winding to a first signal;

set point means for supplying a second signal representative of the predetermined value of the maximum acceptable leakage current;

amplifying means receptive of the first and second signals and operative for amplifying the difference in magnitude of the first and second signals and for supplying the resultant signal as a third signal; and selector means receptive of the power control signal and the third signal and operative for supplying the larger one of the power control or third signal to the regulating means of the power control feedback loop means.

6. An invention as defined in claim 5 wherein:
the first and second windings are wound in opposite directions around the core.

7. A method of limiting the electrosurgical power applied to an active electrode in an electrosurgical system to avoid leakage currents of magnitudes greater than a predetermined maximum acceptable level, comprising:

selecting a predetermined level of electrosurgical output power requested for delivery during electrosurgery;

generating electrosurgical output power in response to the predetermined power level requested;

supplying the electrosurgical output power generated by delivering current to the active electrode and receiving return current from a dispersive electrode;

sensing the amount of electrosurgical output power supplied to the active electrode;

determining any output power difference between the electrosurgical output power supplied and the predetermined output power level requested;

sensing any imbalance between the amount of current supplied and received;

determining whether the imbalance exceeds a predetermined amount representative of a predetermined maximum level of acceptable leakage current; and selectively regulating the output power supplied in relation to both of any imbalance and any output power difference by reducing the level of the electrosurgical output power supplied when the imbalance exceeds the predetermined maximum level of acceptable leakage current and by maintaining the imbalance at or below the predetermined maximum acceptable level when generating power in response to any output power difference.

8. A method as defined in claim 7, wherein the step of selectively regulating the power generated further includes limiting the output power supplied to a predetermined maximum value at which the leakage current does not exceed the predetermined maximum acceptable level.

9. A method as defined in claim 7, wherein the step of selectively regulating the power generated further includes maintaining the amount of electrosurgical output power supplied to a value at which the leakage current does not exceed the predetermined maximum acceptable level.

* * * * *